(12) United States Patent
Chiu et al.

(10) Patent No.: US 6,384,060 B1
(45) Date of Patent: May 7, 2002

(54) 2,4,6-TRISBSTITUTED PYRIDINES WITH ESTROGENIC ACTIVITY AND METHODS FOR THE SOLID PHASE SYNTHESIS THEREOF

(75) Inventors: Chingfan Chiu, Hsinchu (TW); Zhilian Tang, Edgewater; John W. Ellingboe, Ridgewood, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/703,297

(22) Filed: Nov. 1, 2000

Related U.S. Application Data

(62) Division of application No. 09/209,663, filed on Dec. 10, 1998.
(60) Provisional application No. 60/109,802, filed on Dec. 11, 1997.

(51) Int. Cl.[7] .................... C07D 405/04; A61K 31/443
(52) U.S. Cl. ................. 514/338; 514/336; 514/277; 514/332; 546/283.4; 546/257; 546/256
(58) Field of Search ................ 546/283.7; 514/338

(56) References Cited

U.S. PATENT DOCUMENTS

| | | | |
|---|---|---|---|
| 4,831,030 A | 5/1989 | Takasugi | 514/252 |
| 4,931,453 A | 6/1990 | Takasugi | 514/252 |
| 4,990,507 A | 2/1991 | Takaya | 514/227.8 |

FOREIGN PATENT DOCUMENTS

| | | | |
|---|---|---|---|
| EP | 02288845 B1 * | 7/1987 |
| EP | 02288845 A3 * | 7/1987 |
| EP | 02288845 A2 * | 7/1987 |
| EP | 0311322 A2 | 12/1989 |
| EP | 0311322 B1 | 12/1989 |
| EP | 0311322 A3 | 12/1989 |
| JP | 179155 A | 3/1989 |
| JP | 62149662 A | 3/1989 |
| WO | 8911279 | 11/1989 |
| WO | 9427604 | 8/1994 |
| WO | 9621656 | 9/1995 |
| WO | 9600213 | 4/1996 |
| WO | 9616942 | 5/1996 |

OTHER PUBLICATIONS

Borman, S. Chemical and Engineering News, 1997, 75 (8), 43–62.
Gordeev, M.F. et al, Tetrahedron Lett., 1996, 37, 4643–4646.
Hermkens, P.H.H.;Ottenheijm, H.C.J; Rees, D. Tetrahedron 1996, 52, 4527–4554.
Olekhnovich, E.P. et al., Russ. J. Org. Chemistry. (English Transl.) 32, 190 7, 1055–1058 (1996).
Tzukerman, M.T., Esty, A., Santiso–Mere, D. Danielian, P. Parker, M.G., Stein, R.B., Pike, J.W. and McDonnell, D.P. Molecular Endocrinology 1994, 8, 21–30.
Drewes, S.E. et al., J. Chem. Soc . . . , Perkin Trans I, 1989.
Karle, et al. Antimicrob. Agents Chemother. 1989, 33, 1081–1089.
Katritzky, A.R. Handbook of Heterocyclic Chemistry, pp. 408–409, Pergammon Press: Oxford, 1985.
Krohnke, F., Synthesis, 1976, 1–25.
Wang, S.; J. Am. Chem. Soc. 1973, 95, 1328–1333.
Dilthey, W. et al., J. Prakt. Chem. 114 153–178 (1926) C.A. 21:410–411 (English Abstract of J. Prakt. Chem.).
Dilthey, W. et al., J.Prakt. Chem. 104, 28–36 C.A. 17:762 (English Abstract of J.Prakt Chem.).*
Dithey, W. et al., J.Prakt Chem. 102, 209–240 (1921) C.A. 15:3843–3845 (English Abstract.).*

* cited by examiner

Primary Examiner—Jane Fan
(74) Attorney, Agent, or Firm—Daniel B. Moran

(57) ABSTRACT

The present invention relates to novel substituted pyridine compounds of Formula (I)

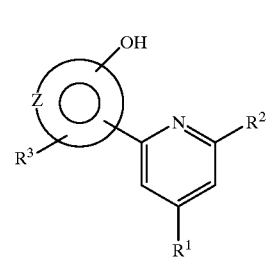

(I)

wherein the moiety Z, $R^1$, $R^2$ and $R^3$ are as herein defined, having estrogenic activity, to processes for their preparation, to a combinatorial library and solid phase methods for preparing libraries of the compounds, to utilizing libraries of the compounds for drug discovery, to methods of treatment and to pharmaceutical compositions thereof.

8 Claims, No Drawings

2,4,6-TRISBSTITUTED PYRIDINES WITH ESTROGENIC ACTIVITY AND METHODS FOR THE SOLID PHASE SYNTHESIS THEREOF

This application is a div of 09/209,663 claims the benefit of U.S. Provisional Application No. 60/109,802, which was converted from U.S. patent application Ser. No. 08/989,057, filed Dec. 11, 1997, pursuant to a petition filed under 37 C.F.R. 1.53(c) (2) on Jul. 10, 1998.

FIELD OF THE INVENTION

The present invention relates to novel substituted pyridine compounds having estrogenic activity, to processes for their preparation, to combinatorial and solid phase methods for preparing libraries of the compounds, to utilizing libraries of the compounds for drug discovery, to methods of treatment and to pharmaceutical compositions thereof.

BACKGROUND OF THE INVENTION

The solid phase synthesis. of non-peptidic small organic molecules is a rapidly evolving area of research with applications in the preparation of combinatorial libraries. While the solid phase synthesis of peptides is an established, the solid phase synthesis of non-peptidic small organic molecules is still evolving (Hermkens, P. H. H.; Ottenheijm, H. C. J.; Rees, D. Tetrahedron 1996, 52, 4527–4554). In particular, methods for the solid phase synthesis of heterocyclic ring systems of importance to drug discovery is an active area of research.

Pyridine derivatives are commonly used as pharmaceuticals (Gordeev, M. F., et al. Tetrahedron Lett., 1996, 37, 4643–4646). Trisubstituted pyridines are a useful class of compounds. Karle, et al. (Antimicrob. Agents Chemother. 1989, 33, 1081–1089) describe 2,4,6-trisubstituted pyridines as antiprotozoal agents. Shirai, et al. (WO 96/00213) describe 2,4,6-trisubstituted pyridines as useful for accelerating nerve growth factor production, and also ((WO 96/16942) as useful for ameliorating neuropathy.

Combinatorial chemistry is becoming an important tool for drug discovery and lead optimization (Borman, S. Chemical and Engineering News 1997, 75 (8), 43–62). A combinatorial synthesis requires that at least two components of the product molecules be independently variable, so that all of the combinations of these components can be prepared. A synthesis with three independently variable components is preferable since greater diversity in structure can be produced in the resultant library. Thus, to prepare a combinatorial library of pyridines with a high degree of potential diversity and wide utility for drug discovery using solid phase techniques, it is important to identify a pyridine synthesis in which three components can be independently varied. The solution phase synthesis of pyridines from 1,5-pentanediones and amnonia followed by oxidation is known (Katritzky, A. R. Handbook of Heterocyclic Chemistry, pp. 408–409; Pergamon Press: Oxford, 1985). A variation of this synthesis involves the reaction of a bromomethyl ketone with pyridine, and subsequent reaction of this intermediate with an unsaturated ketone in the presence of ammonium acetate in acetic acid to yield a 2,4,6-trisubstituted pyridine (Krohnke, F. Synthesis 1976, 1–24). The latter synthesis proceeds through a 1,5-diketone intermediate which is not isolated. For a solid phase combinatorial synthesis it is necessary to modify these syntheses to allow for the independent introduction of three variables (the 2,4, and 6 substituents), and to adapt the solution phase synthesis to a solid supported synthesis. The solid phase pyridine synthesis of this invention is achieved by using a hydroxyacetophenone starting material which can be attached to a solid support through the phenolic hydroxy group.

A solid phase synthesis of 2,3,4,5,6-pentasubstituted dihydropyridines and pyridines has been described in Gordeev, M. F., et al. Tetrahedron Lett., 1996, 37, 4643–4646. The compounds are prepared by the Hantzsch pyridine synthesis and therefore all contain acyl or carboxyl groups in the 3- and 5-positions. The solid phase synthesis of the current invention does not yield pyridines with acyl or carboxyl groups in the 3- and 5-position of all products and therefore yields a more diverse set of products.

Multiple compounds can be prepared simultaneously by the solid phase process. The simultaneous solid phase synthesis of a library of 2,4,6-trisubstituted pyridines of the present invention is not known. The preparation of libraries of compounds of the present invention is useful because it provides rapid structural variation and structure-activity information.

The libraries of substituted pyridines synthesized according to the present invention are useful for drug discovery. Screening of the pyridine libraries in an estrogen receptor assay identified compounds with estrogen agonist activity. Estrogen agonists are useful as post-menopausal therapeutics for the prevention and treatment of osteoporosis, atherosclerosis, and Alzheimer's disease.

SUMMARY OF THE INVENTION

The present invention relates to new compounds selected from those of the general Formula (I) and also discloses a solid phase synthesis process for producing new compounds selected from those of Formula (I):

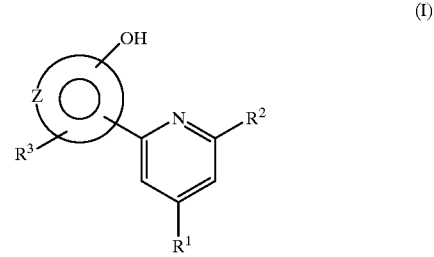

wherein:
the moiety Z

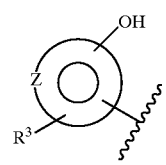

is selected from the group:

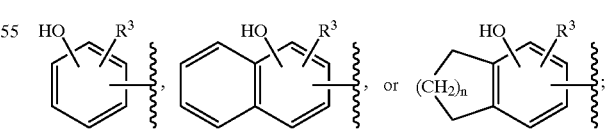

n is an integer of 1 or 2;
$R^1$ is straight chain alkyl of 1 to 6 carbon atoms, branched chain alkyl of 3 to 7 carbon atoms, cycloalkyl of 3 to 7 carbon atoms, phenyl, or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, phenyl, alkoxy of 1 to 6 carbon atoms, or methylenedioxy;

$R^2$ is furanyl, pyridyl, thienyl, naphthalenyl, phenyl, or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, alkoxy of 1 to 6 carbon atoms, or methylenedioxy;

$R^3$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

and all crystalline forms and the pharmaceutically acceptable salts thereof, the enantiomers thereof, the racemic mixtures thereof, and the diastereomeric mixtures thereof.

Among the preferred groups of compounds of this invention are those in the subgroups:

a) compounds having the general formula:

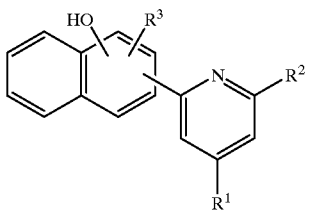

wherein $R^1$, $R^2$, and $R^3$ are as defined above or a pharmaceutically acceptable salt;

b) compounds having the general formula:

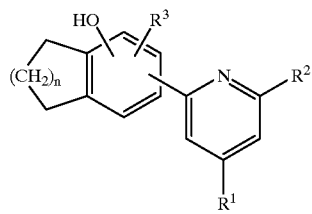

wherein $R^1$, $R^2$, $R^3$ and n are as defined above or a pharmaceutically acceptable salt.

Among the more preferred compounds of this invention are those of the formula:

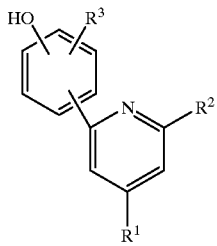

wherein $R^1$, $R^2$, and $R^3$ are as defined above or a pharmaceutically acceptable salt.

The most particularly preferred compounds of Formula (I) of the present invention prepared by the herein described solid phase synthesis processes are:

2-[6-(4-chloro-phenyl)-4-(3,4-difluoro-phenyl)-pyridin-2-yl]-phenol or a pharmaceutically acceptable salt thereof;

2-[4-(3,4-difluoro-phenyl)-6-naphthalen-2-yl-pyridin-2-yl]-phenol or a pharmaceutically acceptable salt thereof;

2-[4-(3,4-difluoro-phenyl)-6-furan-2-yl-pyridin-2-yl]-phenol or a pharmaceutically acceptable salt thereof;

2-(4-benzo[1,3]dioxol-5-yl-6-naphthalen-2-yl-pyridin-2-yl)-phenol or a pharmaceutically acceptable salt thereof;

2-(4-benzo[1,3]dioxol-5-yl-6-thiophen-3-yl-pyridin-2-yl)-phenol or a pharmaceutically acceptable salt thereof;

2-(4-biphenyl-4-yl-6-naphthalen-2-yl-pyridin-2-yl)-4-fluoro-phenol or a pharmaceutically acceptable salt thereof;

2-(4-biphenyl-4-yl-[2,4]bipyridinyl-6-yl)-4-fluoro-phenol or a pharmaceutically acceptable salt thereof;

2-(4-cyclohexyl-6-furan-2-yl-pyridin-2-yl)-4-fluoro-phenol or a pharmaceutically acceptable salt thereof;

3-(4-biphenyl-4-yl-6-naphthalen-2-yl-pyridin-2-yl)-phenol or a pharmaceutically acceptable salt thereof;

3-(4-cyclohexyl-6-furan-2-yl-pyridin-2-yl)-phenol or a pharmaceutically acceptable salt thereof.

The novel process for producing novel compounds of Formula (I) comprises the steps of:

a) attaching a hydroxyacetophenone 1 of the formula

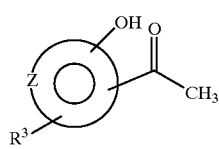

1 or an alkaline metal salt thereof where the moiety Z and $R^3$ are hereinbefore defined, to a solid support to produce an acetophenone 2

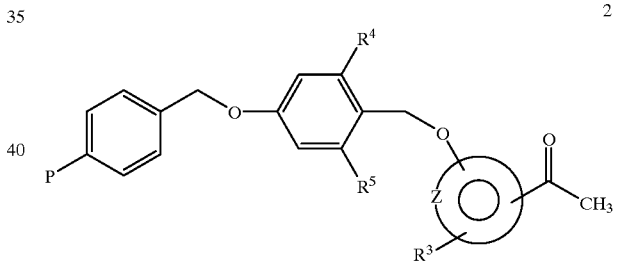

2 wherein the moiety Z and $R^3$ are hereinbefore defined, $R^4$ and $R^5$ are independently hydrogen or methoxy, and P is preferably a polystyrene resin support crosslinked with divinylbenzene;

b) reacting said acetophenone 2 with an aldehyde $R^1$CHO wherein $R^1$ is as hereinbefore defined, in the presence of a base to produce an olefin 3

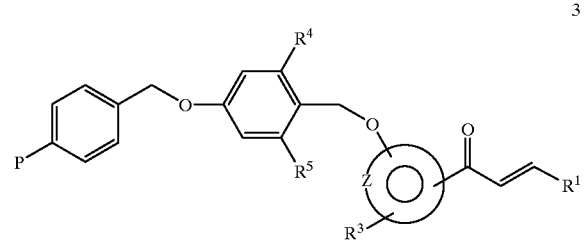

3 wherein the moiety Z, $R^1$, $R^3$, $R^4$, $R^5$, and P are as hereinbefore defined;

c) reacting olefin 3 with a silyl enol ether 4

wherein $R^2$ is as hereinbefore defined and TMS is trimethylsilyl, in the presence of a fluoride source such as cesium fluoride to produce 1,5-diketone 5

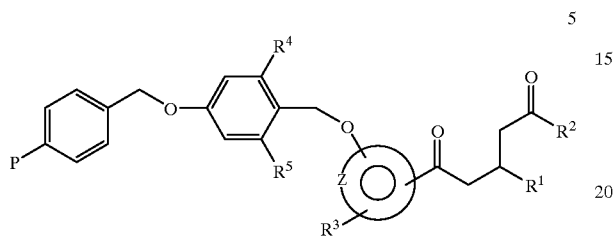

wherein the moiety Z, $R^1$, $R^2$, $R^3$, $R^4$, $R^5$ and P are as hereinbefore defined;

d) reacting 1,5-diketone 5 with ammonium acetate to produce pyridine 6

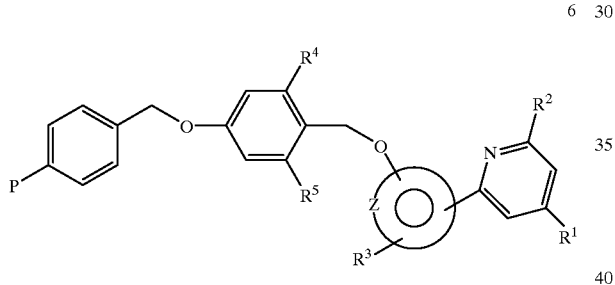

wherein the moiety Z, $R^1$, $R^2$, $R^3$, $R^4$, $R^5$ and P are as hereinbefore defined; and e) reacting pyridine 6 with a cleaving reagent such as trifluoroacetic acid to produce a compound of Formula (I)

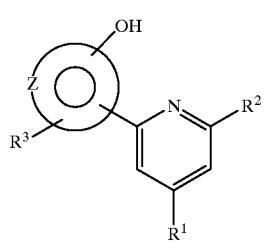

wherein the moiety Z, $R^1$, $R^2$ and $R^3$ are as hereinbefore defined.

The present invention also relates to new combinatorial compound libraries selected from those of the general Formula (I) and also discloses a solid phase synthesis process for producing new compound combinatorial libraries selected from those of Formula (I):

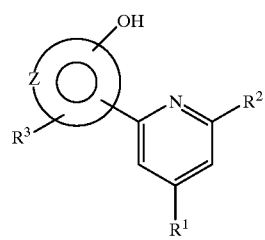

wherein:

the moiety Z

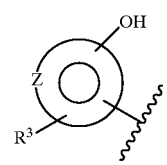

is selected from the group:

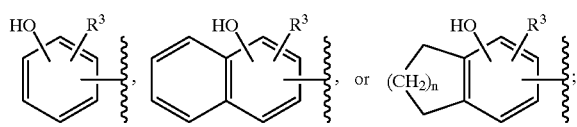

n is an integer of 1 or 2;

$R^1$ is straight chain alkyl of 1 to 6 carbon atoms, branched chain alkyl of 3 to 7 carbon atoms, cycloalkyl of 3 to 7 carbon atoms, phenyl, or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, phenyl, alkoxy of 1 to 6 carbon atoms, or methylenedioxy;

$R^2$ is furanyl, pyridyl, thienyl, naphthalenyl, phenyl, or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, alkoxy of 1 to 6 carbon atoms, or methylenedioxy;

$R^3$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

and all crystalline forms and the pharmaceutically acceptable salts thereof, the enantiomers thereof, the racemic mixtures thereof, and the diastereomeric mixtures thereof.

Among the preferred combinatorial libraries of compounds of this invention are those in the subgroups:

a) combinatorial libraries of compounds having the general formula:

7

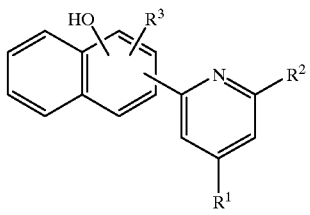

wherein R¹, R², and R³ are as defined above or a pharmaceutically acceptable salt;

b) combinatorial libraries of compounds having the general formula:

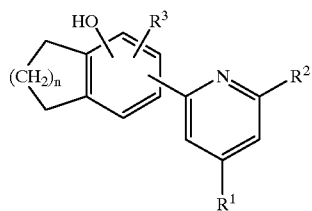

wherein R¹, R², R³ and n are as defined above or a pharmaceutically acceptable salt.

Among the more preferred combinatorial libraries of compounds of this invention are those of the formula:

8

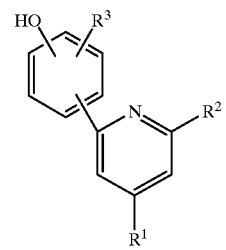

wherein R¹, R², and R³ are as defined above or a pharmaceutically acceptable salt.

It is understood that the definition of the compounds of Formula (I), when R¹, R², and R³ contain asymmetric carbons, encompasses all possible stereoisomers and mixtures thereof. In particular, it encompasses racemic modifications and any optical isomers. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Carboxylic acid salts of the compounds of this invention may be formed with bases such as alkali metals (Na, K, Li) or the alkaline earth metals (Ca or Mg).

DETAILED DESCRIPTION OF THE INVENTION

The compounds of the present invention may be prepared according to the general process outlined below in Scheme I.

SCHEME I

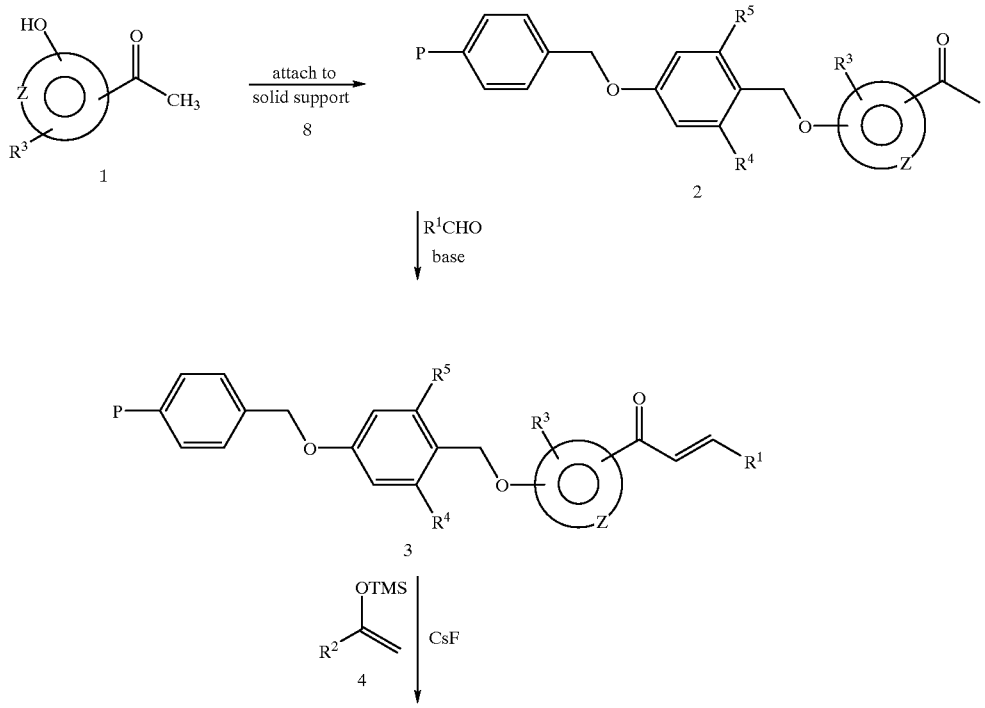

-continued

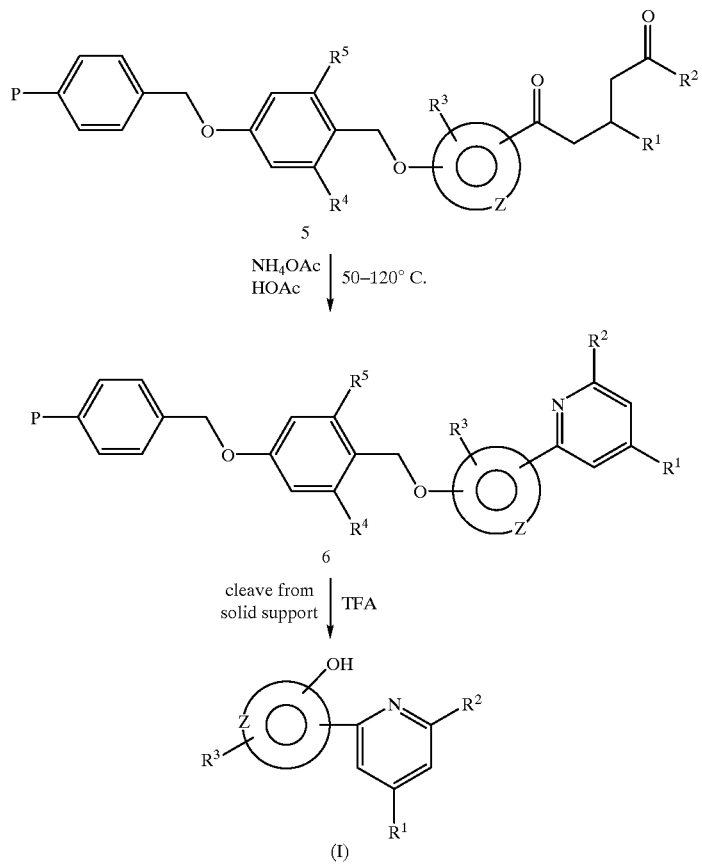

As shown in Scheme II a resin such as Wang resin 7 ($R^4$ and $R^5$=H, P=polystyrene crosslinked with divinylbenzene) (Wang S.; *J. Am. Chem. Soc.* 1973, 95, 1328–1333) is converted to a chloro resin 8 with lithium chloride, methanesulfonyl chloride, and a base such as collidine or lutidine in a polar aprotic solvent such as dimethylformamide.

SCHEME II

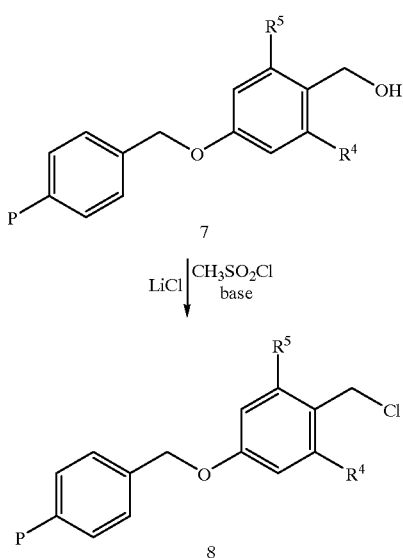

As outlined in Scheme I, chlororesin 8 is reacted with an alkaline metal salt, preferably the cesium salt, of a hydroxy-acetophenone 1 where $R^3$ is hereinbefore defined, to produce an acetophenone 2 where the moiety Z, $R^3$, $R^4$, $R^5$ and P are hereinbefore defined. Acetophenone 2 is reacted with an aldehyde $R^1$CHO where $R^1$ is hereinbefore defined in the presence of a base such as sodium methoxide in a polar aprotic solvent such as trimethyl orthoformate at temperatures ranging from 0° C. to 50° C. to yield an olefin 3 on a solid support resin where the moiety Z, $R^1$, $R^3$, $R^4$, $R^5$ and P are hereinbefore defined. Olefin 3 is reacted with a silyl enol ether 4 where $R^2$ is hereinbefore defined and TMS is trimethylsilyl in the presence of a fluoride source such as cesium fluoride in a polar aprotic solvent such as dimethyl sulfoxide at temperatures ranging from 25° C. to 120° C. to yield a 1,5-diketone 5 on a solid support where the moiety Z, $R^1$, $R^2$, $R^3$, $R^4$, $R^5$ and P are hereinbefore defined. A 1,5-diketone 5 is reacted with ammonium acetate in the presence of acetic acid in a polar aprotic solvent such as dimethylformamide at temperatures ranging from 25° C. to 120° C. to yield a pyridine 6 on a solid support where the moiety Z, $R^1$, $R^2$, $R^3$, $R^4$, $R^5$ and P are hereinbefore defined. A compound of Formula (I) where the moiety Z, $R^1$, $R^2$ and $R^3$ are as defined above is removed from the solid support with an acidic cleavage mixture such as trifluoroacetic acid in dichloromethane.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patient suffering from heart failure.

It is understood that the dosage, regimen and mode of administration of these compounds will vary according to the malady and the individual being treated and will be subject to the judgement of the medical practitioner involved. It is preferred that the administration of one or more of the compounds herein begin at a low dose and be increased until the desired effects are achieved.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and beta-blocking agents.

The new compounds of Formula (I) of this invention are useful in treating conditions in mammals characterized by estrogen deficiency such as in post-menopausal women.

In particular, compounds of Formula (I) of this invention are useful as post-menopausal therapeutics for the prevention and treatment of osteoporosis, atherosclerosis, and Alzheimer's disease in mammals.

The present invention further provides a compound of the invention for use as an active therapeutic substance.

Estrogen Receptor Assay: 2×VIT ERE Transfection Assay
Objective

To identify compounds that enhance the expression of luciferase gene activity compared to 17B-estradiol in a transient transfection model. Enhancement of luciferase gene expression in this model is dependent upon estrogen receptor (ER) interaction with a vitellogenin gene estrogen responsive element (ERE) capable of enhancing basal promoter activity. This is a sensitive and rapid methodology to assess estrogenic/antiestrogenic potency of compounds.

Procedure

Cell Maintenace and treatment: Chinese Hamster Ovary cells (CHO) which have been stably transfected with the human estrogen receptor are maintained in DMEM+10% fetal bovine serum (FBS). 48 h prior to treatment the growth medium is replaced with DMEM lacking phenol red+10% dextran coated charcoal stripped FBS (treatment medium). Cells are plated at a density of 5000 cells/well in 96-well plates containing 200 µL of medium/well.

Calcium Phosphate Transfection

Reporter DNA (Promega plasmid pGL2 containing two tandem copies of the vitellogenin ERE in front of the minimal thymidine kinase promoter driving the luciferase gene) is combined with the B-galactosidase expression plasmid pCH110 (Pharmacia) and carrier DNA (pTZ18U) in the following ratio: 10 µg of reporter DNA, 5 µg of pCH110 DNA, 5 µg of pTZ18U, and 20 µg of DNA/1 mL of transfection solution. The DNA (20 µg) is dissolved in 500 µL of 250 mM sterile $CaCl_2$ which is then slowly (dropwise) added to 500 µL of 2×HeBS (0.28 M NaCl, 50 mM HEPES, 1.5 mM $Na_2HPO_4$, pH 7.05) and incubated at room temperature for 20 min. 20 µL of this mixture is added to each well of cells and remains on the cells for 16 h. At the end of this incubation the precipitate is removed, the cells are washed with media, fresh treatment media is replaced and the cells are treated with either vehicle, 1 nM 17B-estradiol, 1 µM compound or 1 µM compound+1 nM 17B-estradiol. Each treatment condition is performed on 8 wells (n=8) which are incubated for 24 h prior to luciferase assay.

Luciferase Assay

After 24 h exposure to compounds, the media is removed and each well is washed 2× with 125 µL of PBS lacking Mg++ and Ca++. After removing the PBS, 25 µL of Promega lysis buffer is added to each well and allowed to stand at room temperature for 15 min, followed by 15 min at −80 deg. C. and 15 min at 37 degC. 20 µL of lysate is tranferred to an opaque 96-well plate for luciferase activity evaluation and the remaining lysate (5 µL) is used for B-galactosidase activity evaluation (normalize transfection). The luciferan substrate (Promega) added is 100 µL aliquots to each well automatically by the luminometer and the light produced (relative light units) is read 10 seconds after addition. The data is logged and automatically sent to a JMP statistical program for analysis. A hard copy printout is also produced at the time of the assay.

B-galactosidase Assay

To the remaining 5 µL of lysate 45 µL of PBS is added. 50 µl of Promega B-galactosidase 2×assay buffer is added, mixed well and incubated at 37 deg. C. for 1 h. A plate containing a standard curve (0.1 to 1.5 milliunits in triplicate) is set up for each experimental run. The plates are analyzed on a Molecular Devices spectrophotometric plate reader at 410 nm. The optical densities for the unknowns are converted to milliunits of activity by mathematical extrapolation from the standard curve.

Analysis of Results

The luciferase data is generated as relative light units (RLUs) accumulated during a 10 second measurement and is automatically transferred to a JMP (SAS Inc) file where background RLUs are subtracted. The B-galactosidase values are automatically imported into the file and these values are divided into the RLUs to normalize the data. The mean and standard deviation is determined from a n=8 for each treatment. Compound activity is compared to 17B-estradiol for each plate. Percentage of activity as compared to 17B-estradiol is calculated as follows:

%=((Estradiol value-control value)/(compound value))×100

The results of this assay on representative compounds of this invention are shown in Table I.

TABLE I

Estrogen Receptor Assay 2X VIT ERE Transfection Assay

| EXAMPLE | Estrogenic activity at 1 µM (% of activity of 1 nM 17B-estradiol) |
| --- | --- |
| 1 | 14% |
| 3 | 10% |
| 4 | 22% |
| 7 | 6% |
| 10 | 36% |

Reference Compounds

Various reference compounds (1 µM) were assessed for estrogenic and/or antiestrogenic activity (1 µM compound+1 µM 17B-estradiol) by assaying for luciferase activity and corresponding % values compared to 1 nM 17B-estradiol (set to 100%) were calculated. Note there are three orders of magnitude difference in the dose of reference compounds versus 17B-estradiol concentration:

| | |
|---|---|
| 17B-estradiol | 100% activity |
| estriol | 38% activity |
| estrone | 40% activity |
| tamoxifen (+1 nM estradiol) | <5% activity, (10%) |
| raloxifene (+1 nM estradiol) | <5% activity, (0%) |

At 1 μM dosages the estriol and estrone would be expected to be about 40% as potent as 17B-estradiol in this assay. The lack of independent activity and antiestrogenic activity of tamoxifen and raloxifene was as predicted as consistent with reports in the literature relating to their effects in a rat uterotrophic assay.

Reference: Tzukerman, M. T., Esty, A., Santiso-Mere, D., Danielian, P., Parker, M. G., Stein, R. B., Pike, J. W. and McDonnell, D. P. Human estrogen receptor transactivational capacity is determined by both cellular and promoter context and mediated by two functionally distinct intramolecular regions. *Molecular Endocrinology* 1994, 8, 21–30.

Specific procedures are described in the following experimental examples. These examples are given to illustrate the invention and should not be construed as limiting the invention set forth in the appended claims.

EXAMPLE 1

2-[6-(4-Chloro-phenyl)-4-(3,4-difluoro-phenyl)-pyridin-2-yl]-phenol

Step 1

Chloro-Wang Resin

A mixture of Wang resin (Wang, S. *J. Am. Chem. Soc.* 1973, 95, 1328–1333) (Advanced ChemTech 200–400 mesh, 1% crosslinked; loading: 0.92 mmol/g; 15.0 g, 0.011 mol), LiCl (1.4 g, 0.033 mol) and DMF (150 mL) was magnetically stirred for 40 min. Collidine (4.0 g, 0.033 mol) was added and the mixture was cooled (0–5° C.) with an ice bath. Methanesulfonyl chloride (3.8 g, 0.033 mol) was added over 5 min. After 10 min, the cooling bath was removed and stirring was continued for 68 h. The mixture was filtered and the resin was washed with DMF (250 mL), 30% $H_2O$/DMF ((2×300 mL), DMF (2×250 mL), EtOH (3×250 mL), $CH_2Cl_2$ (3×300 mL), and hexane (2×250 mL). The resin was dried over $P_2O_5$ in vacuo to give 14.3 g; $^{13}C$ NMR ($CDCl_3$) d 46.22 ($CH_2Cl$); IR (KBr) $cm^{-1}$: 2900, 1600,; 1520, 1485, 1450.

Step 2

Attachment of 2-Hydroxyacetophenone to Wang Resin

A mixture of chloro Wang resin (6.0 g, 6.9 mmol), 2-hydroxyacetophenone (34.5 mmol), $Cs_2CO_3$ (6.7 g, 20.7 mmol), and NaI (1.0 g, 6.9 mmol) in DMF (100 mL) was stirred at 50° C. for 5 h. The resin was filtered and washed with 2:1 DMF/$H_2O$, 9:1 DMF/$H_2O$, DMF (×2), and alternating MeOH and $CH_2Cl_2$ (×4). After drying under high vacuum overnight, 2-hydroxyacetophenone on Wang resin (6.78 g) was obtained.

Step 3

Reaction With 3,4-Difluorobenzaldehyde

A mixture of 2-hydroxyacetophenone on Wang resin (2.0 g, 1.76 mmol) was swelled in trimethyl orthoformate (20 mL) for 10 min. 3,4-Difluorobenzaldehyde (6.0 mmol) was added and 25% NaOMe in MeOH (0.86 g, 4.0 mmol) was added to the mixture dropwise over 30 min. The mixture was then stirred for an additional 0.5 h. The resin was filtered and washed with alternating MeOH and $CH_2Cl_2$ (×5) and dried under high vacuum overnight to give 2.17 g of 3-(3,4-difluorophenyl)-1-(2-hydroxyphenyl)-2-propen-1-one on Wang resin.

To confirm that the reactions occured, 2.0 g of resin was treated with 50% TFA/$CH_2Cl_2$ for 1 h, filtered, and the filtrate was concentrated to give 0.307 g of product. Purification by flash chromatography gave 110 mg (24%) of 3-(3,4-difluorophenyl)-1-(2-hydroxyphenyl)-2-propen-1-one as a yellow solid; mp 138–139° C.; IR (KBr) 1640, 1600 $cm^{-1}$; MS [M+1] m/z=261. Anal. calcd for $C_{15}H_{10}F_2O_2$: C, 69.23; H, 3.87; Found: C, 69.31; H, 3.51.

Step 4

Reaction With 1-Trimethylsilyloxy-1-(4-chlorophenyl) ethylene

1-Trimethylsilyloxy-1-(4-chlorophenyl)ethylene (7.0 mmol; prepared according to *J. Chem. Soc., Perkin Trans. I* 1989, 1585) and CsF (0.27 g, 1.76 mmol) were added to a suspension of 3-(3,4-difluorophenyl)-1-(2-hydroxyphenyl)-2-propen-1-one on Wang resin (2.0 g, 1.76 mmol) in dimethyl sulfoxide (30 mL). The reaction mixture was heated to 70° C. for 3 h and the reaction was quenched with 10% AcOH/$CH_2Cl_2$. The resin was filtered, washed with DMF (×2) and alternating MeOH and $CH_2Cl_2$ (×5), and dried under high vacuum overnight to give 3-(3,4-difluorophenyl)-1-(2-hydroxphenyl)-5-(4-chlorophenyl)-1,5-pentanedione on Wang resin.

Step 5

Reaction With Ammonium Acetate

A mixture of 3-(3,4-difluorophenyl)-1-(2-hydroxyphenyl)-5-(4-chlorophenyl)-1,5-pentanedione on Wang resin (2.0 g, 1.76 mmol), $NH_4OAc$ (0.80 g), and AcOH (1.0 mL) in dimethylformamide (20 mL) was heated at 100° C. for 18 h. The resin was filtered, and washed with dimethylformamide (×2) and alternating MeOH and $CH_2Cl_2$ (×5), and dried under high vacuum overnight. The dried resin was treated with 50% TFA/$CH_2Cl_2$ (15 mL) for 1 h. After filtration of the reaction mixture, the filtrate was concentrated to dryness. The residue was repeatedly dissolved in $CH_2Cl_2$ (10 mL) and concentrated to remove traces of TFA, and lyophilized to give 2-[6-(4-chlorophenyl)-4-(3,4-difluoro-phenyl)-pyridin-2-yl]-phenol; mp 146–148° C.; $^1H$ NMR (DMSO-$d_6$) d 6.75 (m, 1H), 7.00 (m, 2H), 7.35 (m, 2H), 7.57 (m, 1H), 7.69 (d, J=8.6 Hz, 2H), 7.95 (d, J=8.6 Hz, 1H), 8.18 (d, J=8.6 Hz, 2H), 8.32 (m, 2H), 14.00 (s, 1H); IR (KBr) 1606 $cm^{-1}$; MS [M+1] m/z=394. Anal. calcd for $C_{23}H_{14}ClF_2NO$: C, 70.15; H, 3.58; N, 3.50; Found: C, 69.98; H, 3.51; N, 1.80.

EXAMPLE 2

2-[4-(3,4-Difluoro-phenyl)-6-naphthalen-2-yl-pridin-2-yl]-phenol

Step 1

Reaction With 1-Trimethylsilyloxy-1-(naphthalen-2-yl-1-phenol 2-yl)ethylene

1-Trimethylsilyloxy-1-(naphthalen-2-yl)ethylene (7.0 mol; prepared according to *J. Chem. Soc., Perkin Trans. I* 1989, 1585) and CsF (0.27 g, 1.76 mmol) were added to a suspension of 3-(3,4-difluorophenyl)-1-(2-hydroxyphenyl)-2-propen-1-one on Wang resin (2.0 g, 1.76 mmol) in dimethyl sulfoxide (30 mL). The reaction mixture was heated to 70° C. for 3 h and the reaction was quenched with 10% AcOR/$CH_2Cl_2$. The resin was filtered, washed with DMF (×2) and alternating MeOH and $CH_2Cl_2$ (×5), and dried under high vacuum overnight to give 3-(3,4-difluorophenyl)-1-(2-hydroxyphenyl)-5-(naphthalen-2-yl)-1,5-pentanedione on Wang resin.

Step 2
Reaction With Ammonium Acetate

A mixture of 3-(3,4-difluorophenyl)-1-(2-hydroxyphenyl)-5-(naphthalen-2-yl)-1,5-pentanedione on Wang resin (2.0 g, 1.76 mmol), NH$_4$OAc (1.0 g), and AcOH (1.5 mL) in dimethylformamide (40 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 2-[4-(3,4-difluoro-phenyl)-6-naphthalen-2-yl-pyridin-2-yl]-phenol; mp 165–167° C.; $^1$H NMR (DMBO-d$_6$) d 6.99 (m, 2H), 7.38 (m, 1H), 7.65 (m, 4H), 8.06 (m, 4H), 8.24 (d, J=6.8 Hz, 1H), 8.42 (m, 2H), 8.49 (d, J=1.2 Hz, 1H), 8.74 (s, 1H), 14.35 (s, 1H); IR (KBr) 1602 cm$^{-1}$; MS [M+H]$^+$ m/z=410. Anal. calcd for C$_{27}$H$_{17}$F$_2$NO: C, 79.21; H, 4.19; N, 3.42; Found: C, 79.33; H, 4.19; N. 3.22.

EXAMPLE 3
2-[4-(3,4-Difluoro-phenyl)-6-furan-2-yl-pyridin-2-yl]-phenol
Step 1
Reaction With 1-Trimethylsilyloxy-1-(furan-2-yl)ethylene 1-Trimethylsilyloxy-1-(furan-2-yl)ethylene (7.0 mmol; prepared according to *J. Chem. Soc., Perkin Trans. I* 1989, 1585) and CsF (0.27 g, 1.76 mmol) were added to a suspension of 3-(3,4-difluorophenyl)-1-(2-hydroxyphenyl)-2-propen-1-one on Wang resin (2.0 g, 1.76 mmol) in dimethyl sulfoxide (30 mL). The reaction mixture was heated to 70° C. for 3 h and the reaction was quenched with 10% AcOH/CH$_2$Cl$_2$. The resin was filtered, washed with DMF (×2) and alternating MeOH and CH$_2$Cl$_2$ (×5), and dried under high vacuum overnight to give 3-(3,4-difluorophenyl)-5-(furan-2-yl)-1-(2-hydroxyphenyl)-1,5-pentanedione on Wang resin.
Step 2
Reaction With Ammonium Acetate A mixture of 3-(3,4-difluorophenyl)-5-(furan-2-yl)-1-(2-hydroxyphenyl)-1,5-pentanedione on Wang resin (2.0 g, 1.76 mmol), NH$_4$OAc (0.80 g), and AcOH (1.0 mL) in dimethylformamide (20 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 2-[4-(3,4-difluoro-phenyl)-6-furan-2-yl-pyridin-2-yl]-phenol; mp 147–148° C.; $^1$H NMR (DMSO-d$_6$) d 6.78 (m, 1H), 6.98 (m, 2H), 7.37 (m, 1H), 7.43 (m, 1H), 7.67 (m, 1H), 8.00 (m, 2H), 8.15 (d, J=1.3 Hz, 1H), 8.31 (m, 2H), 8.39 (d, J=1.3 Hz, 1H), 14.26, (s, 1H); IR (KBr) 1605 cm$^{-1}$; MS [M+H]$^+$ m/z=350. Anal. calcd for C$_{21}$H$_{13}$F$_2$NO$_2$: C, 72.20; H, 3.75; N, 4.01; Found: C, 71.94; H, 3.62; N, 3.74.

EXAMPLE 4
2-(4-Benzo[1,3]dioxol-5-yl-6-naphthalen-2-yl-pyridin-2-yl)-phenol
Step 1
Reaction With 3,4-Methylenedioxy-benzaldehyde A mixture of 2-hydroxyacetophenone on Wang resin (2.0 g, 1.76 mmol) was swelled in trimethyl orthoformate (20 mL) for 10 min. 3,4-Methylenedioxybenzaldehyde (6.0 mmol) was added and 25% NaOMe in MeOH (0.86 g, 4.0 mol) was added to the mixture dropwise over 30 min. The mixture was then stirred for an additional 0.5 h. The resin was filtered and washed with alternating MeOH and CH$_2$Cl$_2$ (×5) and dried under high vacuum overnight to give 2.23 g of 1-(2-hydroxyphenyl)-3-(3,4-methylenedioxphenyl)-2-propen-1-one on Wang resin.

To confirm that the reactions occured, a 2.00 g of resin was treated with 30% TFA/CH$_2$Cl$_2$ for 1 h, filtered, and the filtrate was concentrated to give 369 mg of crude product. Purification by flash chromatography (15% ethyl acetate/hexane) gave 126 mg (27%) of 3-(3,4-difluorophenyl)-1-(2-hydroxyphenyl)-2-propen-1-one as a yellow solid; mp 131–133° C.; IR (KBr) 1640, 1620 cm$^{-1}$; MS [M+1] m/z= 269. Anal. calcd for C$_{16}$H$_{12}$O$_4$: C, 71.60; H, 4.51; Found: C, 71.72; H, 4.26.
Step 2
Reaction With 1-Trimethylsilyloxy-1-(naphthalen-2-yl) ethylene 1-Trimethylsilyloxy-1-(naphthalen-2-yl)ethylene (7.0 mmol; prepared according to *J. Chem. Soc., Perkin Trans. I* 1989, 1585) and CsF (0.27 g, 1.76 mmol) were added to a suspension 1-(2-hydroxyphenyl)-3-(3,4-methylenedioxyphenyl)-2-propen-1-one on Wang resin (2.0 g, 1.76 mmol) in dimethyl sulfoxide (30 mL). The reaction mixture was heated to 70° C. for 3 h and the reaction was quenched with 10% AcOH/CH$_2$Cl$_2$. The resin was filtered, washed with DMF (×2) and alternating MeOH and CH$_2$Cl$_2$ (×5), and dried under high vacuum overnight to give 1-(2-hydroxyphenyl)-3-(3,4-methylenedioxyphenyl)-5-(naphthalen-2-yl)-1,5-pentanedione on Wang resin.
Step 3
Reaction With Ammonium Acetate A mixture of 1-(2-hydroxyphenyl)-3-(3,4-methylenedioxyphenyl)-5-(naphthalen-2-yl)-1,5-pentanedione on Wang resin (2.7 g, 1.68 mmol), NH$_4$OAc (1.0 g), and AcOH (1.5 mL) in dimethylformamide (40 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 2-(4-benzo[1,3]dioxol-5-yl-6-naphthalen-2-yl-pyridin-2-yl)-phenol; mp 195–196° C.; $^1$H NMR (DMSO-d$_6$) d 6.17 (s, 2H), 6.99 (m, 2H), 7.17 (d, J=8.2 Hz, 1H), 7.37 (m, 1H), 7.63 (m, 2H), 7.71 (dd, J=8.2, 1.9 Hz, 1H), 7.83 (d, J=1.8 Hz, 1H), 8.03 (m, 1H), 8.12 (m, 2H), 8.24 (dd, J=8.6, 1.8 Hz, 1H), 8.35 (m, 2H), 8.42 (d, J=1.1 Hz, 1H), 8.74 (s, 1H), 14.55 (s, 1H); IR (KBr) 1605 cm$^{-1}$; MS [M+H]$^+$ m/z=418. Anal. calcd for C$_{28}$H$_{19}$NO$_3$: C, 80.56; H, 4.59; N, 3.36; Found: C, 80.13; H, 4.49; N, 3.18.

EXAMPLE 5
2-(4-Benzo[1,3]dioxol-5-yl-6-thiophen-3-yl-pyridin-2-yl)-phenol
Step 1
Reaction With 1-Trimethylsilyloxy-1-(thiophen-3-yl) ethylene 1-Trimethylsilyloxy-1-(thiophen-3-yl)ethylene (7.0 mmol; prepared according to *J. Chem. Soc., Perkin Trans. I* 1989, 1585) and CsF (0.27 g, 1.76 mmol) were added to a suspension 1-(2-hydroxyphenyl)-3-(3,4-methylenedioxyphenyl)-2-propen-1-one on Wang resin (2.0 g, 1.76 mmol) in dimethyl sulfoxide (30 mL). The reaction mixture was heated to 70° C. for 3 h and the reaction was quenched with 10% AcOH/CH$_2$Cl$_2$. The resin was filtered, washed with DMF (×2) and alternating MeOH and CH$_2$Cl$_2$ (×5), and dried under high vacuum overnight to give 1-(2-hydroxyphenyl)-3-(3,4-methylenedioxyphenyl)-5-(thiophen-3-yl)-1,5-pentanedione on Wang resin.

Step 2
Reaction With Ammonium Acetate

A mixture of 1-(2-hydroxyphenyl)-3-(3,4-methylenedioxyhenyl)-5-(thiophen-3-yl)-1,5-pentanedione on Wang resin (2.0 g, 1.76 mmol), NH$_4$OAc (1.0 g), and AcOH (1.5 mL) in dimethylformamide (40 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 2-(4-benzo[1,3]dioxol-5-yl-6-thiophen-3-yl-pyridin-2-yl)-phenol; mp 120–121° C.; $^1$H NMR (DMSO-d$_6$) d 6.15 (s, 2H), 6.97 (m, 2H), 7.13 (d, J=8.2 Hz, 1H), 7.35 (m, 1H), 7.66 (dd, J=8.2, 1.9 Hz, 1H), 7.80 (m, 3H), 8.16 (d, J=1.1 Hz, 1H), 8.31 (m, 2H), 8.37 (dd, J=2.9, 1.4 Hz, 1H), 14.58 (s, 1H); IR (KBr) 1602 cm$^{-1}$; MS [M+H]$^+$ m/z=374. Anal. calcd for C$_{22}$H$_{15}$NO$_3$S: C, 70.76; H, 4.05; N, 3.75; Found: C, 70.66; H, 4.02; N. 3.59.

EXAMPLE 6
2-(4-Biphenyl-4-yl-6-naphthalen-2-yl-pyridin-2-yl)-4-fluoro-phenol

Step 1
Attachment of 5-Fluoro-2-hydroxyaceto-phenone to Wang Resin

A mixture of chloro Wang resin (6.0 g, 6.9 mmol), 5-fluoro-2-hydroxyacetophenone (5.3 g, 34.5 mmol), CS$_2$CO$_3$ (6.7 g, 20.7 mmol) and NaI (1.0 g, 6.9 mmol) in DMF (100 mL) was stirred at 50° C. for 18 h. The resin was filtered and washed with 2:1 DMF/H$_2$O, 9:1 DMF/H$_2$O, DMF (×2), and alternating MeOH and CH$_2$Cl$_2$ (×4). After drying under high vacuum overnight, 6.72 g of 5-fluoro-2-hydroxyacetophenone on Wang resin was obtained.

Step 2
Reaction With 4-Phenylbenzaldehyde

A mixture of 5-fluoro-2-hydroxyacetophenone on Wang resin (4.0 g, 4.09 mmol) was swelled in trimethyl orthoformate (40 mL) for 10 min. 4-Phenylbenzaldehyde (2.9 g, 16.0 mmol) was added and 25% NaOMe in MeOH (1.77 g, 8.19 mmol) was added to the mixture dropwise over 30 min. The mixture was then stirred for an additional 0.5 h. The resin was filtered and washed with alternating MeOH and CH$_2$Cl$_2$ (×5) and dried under high vacuum overnight to give 4.5 g of 3-biphenyl-1-(2-hydroxy-5-fluorophenyl)-2-propen-1-one on Wang resin.

To confirm that the reactions occured, 106 mg of resin was treated with 50% TFA/CH$_2$Cl$_2$ for 1 h, filtered, and the filtrate was concentrated to give 23.4 mg of 3-biphenyl-1-(2-hydroxy-5-fluorophenyl)-2-propen-1-one; mp 142–144° C.; $^1$H NMR (DMSO-d$_6$) d 6.55 (m, 1H), 7.00 (m, 5H), 7.40 (m, 9H); IR (KBr) 1705, 1650, 1630 cm$^{-1}$; MS (CI) [M+H]$^+$ m/z=319. Anal. calcd for C$_{21}$H$_{15}$ FO$_2$: C, 79.23; H, 4.57; Found: C, 78.71; H, 4.66.

Step 3
Reaction With 1-Trimethylsilyloxy-1-(naphthalen-2-yl) ethylene

1-Trimethylsilyloxy-1-(naphthalen-2-yl)ethylene (2.33 g, 9.57 mmol; prepared according to *J. Chem. Soc., Perkin Trans. I* 1989, 1585) and CsF (0.44 g, 2.87 mmol) were added to a suspension of 3-biphenyl-1-(2-hydroxy-5-fluorophenyl)-2-propen-1-one on Wang resin (2.6 g, 1.8 mmol) in dimethyl sulfoxide (30 mL). The reaction mixture was heated to 70° C. for 3 h and the reaction was quenched with 10% AcOH/CH$_2$Cl$_2$. The resin was filtered, washed with DMF (×2) and alternating MeOH and CH$_2$Cl$_2$ (×5), and dried under high vacuum overnight to give 2.9 g of 3-biphenyl-1-(2-hydroxy-5-fluorophenyl)-5-(naphthalen-2-yl)-1,5-pentanedione on Wang resin.

Step 4
Reaction With Ammonium Acetate

A mixture of 3-biphenyl-1-(2-hydroxy-5-fluorophenyl)-5-(naphthalen-2-yl)-1,5-pentanedione on Wang resin (2.7 g, 1.57 mmol), NH$_4$OAc (1.5 g), and AcOH (1.5 mL) in dimethylformamide (40 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 151 mg (21%) of 2-(4-biphenyl-4-yl-6-naphthalen-2-yl-pyridin-2-yl)-4-fluoro-phenol; mp 187–188° C.; $^1$H NMR (CDCl$_3$) d 7.06 (m, 2H), 7.55 (m, 5H), 7.69 (m, 3H), 7.81 (d, J=8.4 Hz, 2H), 7.89 (m, 4H), 8.03 (m, 4H), 8.12 (dd, J=8.6, 1.8 Hz, 1H), 8.47 (d, J=1.2 Hz, 1H); IR (KBr) 1603 cm$^{-1}$; MS [M+H]$^+$ m/z=468. Anal. calcd for C$_{33}$H$_{22}$FNO: C, 84.78; H, 4.74; N, 3.00; Found: C, 83.98; H, 4.70; N, 2.84.

EXAMPLE 7
2-(4-Biphenyl-4-yl-[2,4']bipyridinyl-6-yl)-4-fluoro-phenol

Step 1
Reaction With 1-Trimethylsilyloxy-1-(pyridin-4-yl)ethylene

1-Trimethylsilyloxy-1-(pyridin-4-yl)ethylene (1.73 g, 8.96 mmol; prepared according to *J. Chem. Soc., Perkin Trans. I* 1989, 1585) and CsF (0.34 g, 2.24 mmol) were added to a suspension of 3-biphenyl-1-(2-hydroxy-5-fluorophenyl)-2-propen-1-one on Wang resin (3.0 g, 2.24 mmol) in dimethyl sulfoxide (40 mL). The reaction mixture was heated to 70° C. for 3 h and the reaction was quenched with 10% AcOH/CH$_2$Cl$_2$. The resin was filtered, washed with DMF (×2) and alternating MeOH and CH$_2$Cl$_2$ (×5), and dried under high vacuum overnight to give 3.46 g of 3-biphenyl-1-(2-hydroxy-5-fluorophenyl)-5-(pyridin-4-yl)-1,5-pentanedione on Wang resin.

Step 2
Reaction With Ammonium Acetate

A mixture of 3-biphenyl-1-(2-hydroxy-5-fluorophenyl)-5-(pyridin-4-yl)-1,5-pentanedione on Wang resin (3.0 g, 2.58 mmol), NH$_4$OAc (2.0 g), and AcOH (3.0 mL) in dimethylformamide (40 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 405 mg (50%) of 2-(4-biphenyl-4-yl-[2,4']bipyridinyl-6-yl)-4-fluoro-phenol; $^1$H NMR (DMSO-d$_6$) d 7.01 (dd, J=9.0, 5.0 Hz, 1H), 7.23 (m, 1H), 7.44 (m, 1H), 7.53 (m, 2H), 7.80 (d, J=7.2 Hz, 2H), 7.90 (d, J=8.4 Hz, 2H), 8.19 (m, 3H), 8.45 (s, 2H), 8.53 (s, 1H), 8.64 (s, 1H), 9.00 (br s, 2H); IR (KBr) 1690, 1640 cm$^{-1}$; MS [M+H]$^+$ m/z=419. Anal. calcd for C$_{33}$H$_{22}$FNO.C$_2$HF$_3$O$_2$: C, 67.67; H, 3.79; N, 5.26; Found: C, 67.42; H, 4.18; N, 5.02.

EXAMPLE 8
2-(4-Cyclohexyl-6-furan-2-yl-pyridin-2-yl)-4-fluoro-phenol
Step 2
Reaction With Cyclohexanecarboxaldehyde A mixture of 5-fluoro-2-hydroxyacetophenone on Wang resin (4.0 g, 4.6 mmol) was swelled in trimethyl orthoformate (40 mL) for 10 min. 25% NaOMe in MeOH (2.0 g, 9.2 mmol) was added and the mixture was stirred for 45 min. Cyclohexanecarboxaldehyde (1.5 g, 13.8 mmol) was added and stirring was continued for 40 min. The resin was filtered and washed with alternating MeOH and $CH_2Cl_2$ (×5) and dried under high vacuum overnight to give 4.3 g of 3-cyclohexyl-1-(2-hydroxy-5-fluorophenyl)-2-propen-1-one on Wang resin.

To confirm that the reactions occured, 100 mg of resin was treated with 50% $TFA/CH_2Cl_2$ for 1 h, filtered, and the filtrate was concentrated to give 25.4 mg of 3-cyclohexyl-1-(2-hydroxy-5-fluorophenyl)-2-propen-1-one; IR (KBr) 1780, 1648, 1627 cm$^{-1}$; MS (CI) [M+H]$^+$ m/z=248. Anal. calcd for $C_{15}H_{17}FO_2.0.5H_2O$: C, 79.23; H, 4.57; Found: C, 78.71; H, 4.66.
Step 3
Reaction With 1-Trimethylsilyloxy-1-(furan-2-yl)ethylene 1-Trimethylsilyloxy-1-(furan-2-yl)ethylene (1.64 g, 9.0 mmol; prepared according to *J. Chem. Soc., Perkin Trans. I* 1989, 1585) and CsF (0.41 g, 2.7 mmol) were added to a suspension of 3-cyclohexyl-1-(2-hydroxy-5-fluorophenyl)-2-propen-1-one on Wang resin (3.0 g, 1.8 mmol) in dimethyl sulfoxide (40 mL). The reaction mixture was heated to 70° C. for 3 h and the reaction was quenched with 10% AcOH/$CH_2Cl_2$. The resin was filtered, washed with DMF (×2) and alternating MeOH and $CH_2Cl_2$ (×5), and dried under high vacuum overnight to give 3.31 g of 3-cyclohexyl-1-(2-hydroxy-5-fluorophenyl)-5-(furan-2-yl)-1,5-pentanedione on Wang resin.
Step 4
Reaction With Ammonium Acetate A mixture of 3-cyclohexyl-1-(2-hydroxy-5-fluorophenyl)-5-(furan-2-yl)-1,5-pentanedione on Wang resin (3.2 g, 1.9 mmol), $NH_4OAc$ (1.8 g), and AcOH (1.8 mL) in dimethylformamide (45 mL) was heated at 100° C. for 18 h. The resin was filtered, and washed with dimethylformamide (×2) and alternating MeOH and $CH_2Cl_2$ (×5), and dried under high vacuum overnight. The dried resin was treated with 50% $TFA/CH_2Cl_2$ (15 mL) for 1 h. After filtration of the reaction mixture, the filtrate was concentrated to dryness. The residue was repeatedly dissolved in $CH_2Cl_2$ (10 mL) and concentrated to remove traces of TFA. Purification by flash chromatography gave 2-(4-cyclohexyl-6-furan-2-yl-pyridin-2-yl)-4-fluoro-phenol; $^1$H NMR (DMSO-d$_6$) d 1.35 (m, 4H), 1.61 (m, 2H), 1.76 (m, 4H), 2.68 (m, 1H), 6.74 (dd, J=3.4, 1.8 Hz, 1H), 6.94 (dd, J=9.0, 5.1 Hz, 1H), 7.18 (m, 1H), 7.26 (d, J=3.4 Hz, 1H), 7.72 (s, 1H), 7.94 (s, 1H), 8.04 (m, 2H), 14.22 (s, 1H); IR (KBr) 1617 cm$^{-1}$; MS [M+H]$^+$ m/z=338. Anal. calcd for $C_{21}H_{20}FNO_2.0.2MCF_3CO_2H$: C, 71.29; H, 5.61; N, 3.89; Found: C, 71.24; H, 5.74; N, 3.76.

EXAMPLE 9
3-(4-Biphenyl-4-yl-6-naphthalen-2-yl-pyridin-2-yl)-phenol
Step 1
Attachment of 3-Hydroxyacetophenone to Wang Resin A mixture of chloro Wang resin (10.0 g, 11.5 mmol), 3-hydroxyacetophenone (7.85 g, 57.5 mmol), $Cs_2CO_3$ (11.4 g, 34.5 mmol) and NaI (1.72 g, 11.5 mmol) in DMF (120 mL) was stirred at 50° C. for 5 h. The resin was filtered and washed with 2:1 DMF/$H_2O$, 9:1 DMF/$H_2O$, DMF (×2), and alternating MeOH and $CH_2Cl_2$ (×4). After drying under high vacuum overnight, 10.88 g of 3-hydroxyacetophenone on Wang resin was obtained.
Step 2
Reaction With 4-Phenylbenzaldehyde A mixture of 3-hydroxyacetophenone on Wang resin (2.0 g, 1.84 mmol) was swelled in trimethyl orthoformate (20 mL) for 10 min; 4-Phenylbenzaldehyde (6.0 mmol) was added and 25% NaOMe in MeOH (0.86 g, 4.0 mmol) was added to the mixture dropwise over 30 min. The mixture was then stirred for an additional 0.5 h. The resin was filtered and washed with alternating MeOH and $CH_2Cl_2$ (×5) and dried under high vacuum overnight to give 2.3 g of 3-biphenyl-1-(3-hydroxyphenyl)-2-propen-1-one on Wang resin.

To confirm that the reactions occured, 100 mg of resin was treated with 50% $TFA/CH_2Cl_2$ for 1 h, filtered, and the filtrate was concentrated to give 22.5 mg of 3-biphenyl-1-(3-hydroxyphenyl)-2-propen-1-one; mp 162–163° C.; $^1$H NMR (DMSO-d$_6$) d 7.07 (dd, J=8.0, 2.2 Hz, 1H), 7.41 (m, 2H), 7.49 (m, 3H), 7.67 (d, J=8.0 Hz, 1H), 7.77 (m, 5H), 7.90 (s, 1H), 8.00 (m, 2H), 9.84 (s, 1H); IR (Kbr) 1652 cm$^{-1}$; MS (CI) [M+H]$^+$ m/z=301. Anal. calcd for $C_{21}H_{16}O_2$: C, 83.98; H, 5.37; Found: C, 83.18; H, 5.42.
Step 3
Reaction With 1-Trimethylsilyloxy-1-(naphthalen-2-yl)ethylene 1-Trimethylsilyloxy-1-(naphthalen-2-yl)ethylene (1.1 g, 4.5 mmol; prepared according to *J. Chem. Soc., Perkin Trans. I* 1989, 1585) and CsF (0.23 g, 1.5 mmol) were added to a suspension of 3-biphenyl-1-(3-hydroxyphenyl)-2-propen-1-one on Wang resin (2.0 g, 1.5 mmol) in dimethyl sulfoxide (30 mL). The reaction mixture was heated to 70° C. for 3 h and the reaction was quenched with 10% AcOH/$CH_2Cl_2$. The resin was filtered, washed with DMF (×2) and alternating MeOH and $CH_2Cl_2$ (×5), and dried under high vacuum overnight to give 2.2 g of 3-biphenyl-1-(3-hydroxyphenyl)-5-(naphthalen-2-yl)-1,5-pentanedione on Wang resin.
Step 4
Reaction With Ammonium Acetate A mixture of 3-biphenyl-1-(3-hydroxyphenyl)-5-(naphthalen-2-yl)-1,5-pentanedione on Wang resin (2.0 g, 1.10 mmol), $NH_4OAc$ (1.0 g), and AcOH (1.0 mL) in dimethylformamide (30 mL) was heated at 100° C. for 18 h. The resin was filtered, and washed with dimethylformamide (×2) and alternating MeOH and $CH_2Cl_2$ (×5), and dried under high vacuum overnight. The dried resin was treated with 50% $TFA/CH_2Cl_2$ (15 mL) for 1 h. After filtration of the reaction mixture, the filtrate was concentrated to dryness. The residue was repeatedly dissolved in $CH_2Cl_2$ (10 mL) and concentrated to remove traces of TFA. Purification by flash chromatography (15% ethyl acetate/hexane) gave 3-(4-biphenyl-4-yl-6-naphthalen-2-yl-pyridin-2-yl)-phenol; mp 174–175° C.; $^1$H NMR (DMSO-d$_6$) d 6.91 (m, 1H), 7.43 (m, 2H), 7.60 (m, 4H), 7.80 (m, 4H), 7.90 (d, J=8.4 Hz, 2H), 8.00 (m, 1H), 8.12 (m, 2H), 8.21 (d, J=8.4 Hz, 2H), 8.44 (d, J=1.1 Hz, 1H), 8.54 (dd, J=8.6, 1.7 Hz, 1H), 8.93 (s, 1H), 9.64 (s, 1H); IR (KBr) 1590 cm$^{-1}$; MS [M+H]$^+$ m/z=450. Anal. calcd for $C_{33}H_{23}NO.H_2O$: C, 84.77; H, 5.39; N, 3.00; Found: C, 85.23; H, 5.39; N, 2.83.

EXAMPLE 10
3-(4-Cyclohexyl-6-furan-2-yl-pyridin-2-yl)-phenol
Step 1
Reaction With Cyclohexanecarboxaldehyde A mixture of 3-hydroxyacetophenone on Wang resin (6.0 g, 5.52 mmol) was swelled in trimethyl orthoformate (60 mL) for 10 min. 25% NaOMe in MeOH (2.4 g, 11.0 mmol) was added and the mixture was stirred for 40 min. Cyclohexanecarboxaldehyde (1.9 g, 16.56 mmol) was added and stirring was continued for 40 min. The resin was filtered and washed with alternating MeOH and CH$_2$Cl$_2$ (×5) and dried under high vacuum overnight to give 6.62 g of 3-cyclohexyl-1-(3-hydroxyphenyl)-2-propen-1-one on Wang resin.

To confirm that the reactions occured, 100 mg of resin was treated with 50% TFA/CH$_2$Cl$_2$ for 1 h, filtered, and the filtrate was concentrated to give 16.1 mg of 3-cyclohexyl-1-(3-hydroxyphenyl)-2-propen-1-one.0.4 ethyl acetate; IR (KBr) 1660 cm$^{-1}$; MS (CI) [M+H]$^+$ m/z=231. Anal. calcd for C$_{15}$H$_{18}$O$_2$.0.4C$_4$H$_8$O$_2$: C, 75.03; H, 7.98; Found: C, 75.14; H, 8.14.

Step 2

Reaction With 1-Trimethylsilyloxy-1-(furan-2-yl)ethylene

1-Trimethylsilyloxy-1-(furan-2-yl)ethylene (1.66 g, 9.1 mmol; prepared according to *J. Chem. Soc., Perkin Trans. I* 1989, 1585) and CsF (0.41 g, 2.7 mmol) were added to a suspension of 3-cyclohexyl-1-(3-hydroxyphenyl)-2-propen-1-one on Wang resin (2.6 g, 1.82 mmol) in dimethyl sulfoxide (30 mL). The reaction mixture was heated to 70° C. for 3 h and the reaction was quenched with 10% AcOH/CH$_2$Cl$_2$. The resin was filtered, washed with DMF (×2) and alternating MeQH and CH$_2$Cl$_2$ (×5), and dried under high vacuum overnight to give 2.7 g of 3-cyclohexyl-1-(3-hydroxyphenyl)-5-(furan-2-yl)-1,5-pentanedione on Wang resin.

Step 3

Reaction With Ammonium Acetate

A mixture of 3-cyclohexyl-1-(3-hydroxyphenyl)-5-(furan-2-yl)-1,5-pentanedione on Wang resin (2.7 g, 1.90 mmol), NH$_4$OAc (1.7 g), and AcOH (1.7 mL) in dimethylformamide (30 mL) was heated at 100° C. for 18 h. The resin was filtered, and washed with dimethylformamide (×2) and alternating MeOH and CH$_2$Cl$_2$ (×5), and dried under high vacuum overnight. The dried resin was treated with 50% TFA/CH$_2$Cl$_2$ (15 mL) for 1 h. After filtration of the reaction mixture, the filtrate was concentrated to dryness. The residue was repeatedly dissolved in CH$_2$Cl$_2$ (10 mL) and concentrated to remove traces of TFA. Purification by flash chromatography gave 3-(4-cyclohexyl-6-furan-2-yl-pyridin-2-yl)-phenol; $^1$H NMR (DMSO-d$_6$) d 1.42 (m, 4H), 1.71 (m, 2H), 1.85 (m, 4H), 2.64 (m, 1H), 6.67 (dd, J=3.3, 1.5 Hz, 1H), 6.85 (dd, J=8.1, 1.8 Hz, 1H), 7.18 (d, J=3.3 Hz, 1H), 7.29 (m, 1H), 7.57 (m, 3H), 7.63 (s, 1H), 7.85 (s, 1H), 9.54 (s, 1H); IR (KBr) 1607 cm$^{-1}$; MS [M+H]$^+$ m/z=320. Anal. calcd for C$_{21}$H$_{21}$NO$_2$.0.6 C$_4$H$_8$O$_2$: C, 75.52; H, 6.94; N, 3.77; Found: C, 75.72; H, 6.72; N, 3.55.

We claim:

1. A compound of Formula (I):

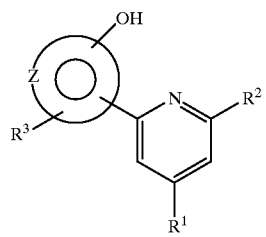

(I)

wherein:

the moiety

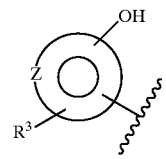

is selected from the group:

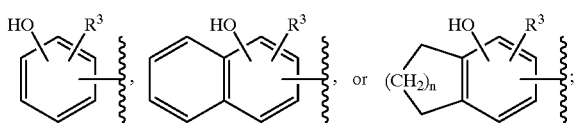

n is an integer of 1 or 2, $R^1$ is phenyl substituted with methylenedioxy;

$R^2$ is thienyl, naphthalenyl, phenyl, or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, alkoxy of 1 to 6 carbon atoms, or methylenedioxy;

$R^3$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, or alkoxy of 1 to 6 carbon atoms;

provided when the moiety:

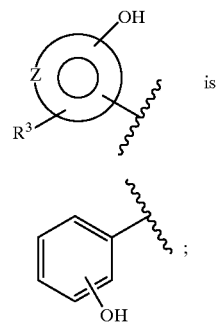

that, $R^2$ is not phenyl or phenyl substituted with halogen, alkoxy or alkyl and all crystalline forms or a pharmaceutically acceptable salt thereof, an enantiomer thereof, a racemate thereof.

2. A compound of claim 1 which is 2-(4-benzo[1,3]dioxol-5-yl-6-naphthalen-2-yl-pyridin-2-yl)-phenol or a pharmaceutically acceptable salt thereof.

3. A compound of claim 1 which is 2-(4-benzo[1,3]dioxol-5-yl-6-thiophen-3-yl-pyridin-2-yl)-phenol or a pharmaceutically acceptable salt thereof.

4. A compound according to claim 1 wherein the formula is:

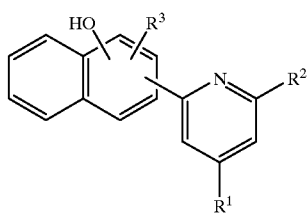

or a pharmaceutically acceptable salt thereof.

5. A compound according to claim 1 wherein the formula is:

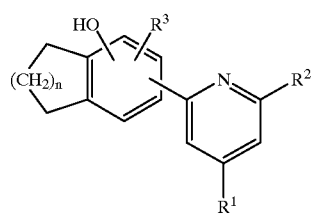

or a pharmaceutically acceptable salt thereof.

6. A compound according to claim 1 wherein the formula is:

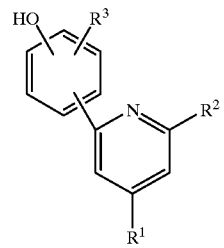

or a pharmaceutically acceptable salt.

7. A pharmaceutical composition which comprises a pharmaceutically acceptable carrier and a therapeutically effective amount of a compound according to claim 1.

8. A method of treating conditions associated with estrogen deficiency in a mammal which comprises administration to a mammal in need thereof a therapeutically effective amount of a compound according to claim 1.

* * * * *